US010407352B2

(12) United States Patent
Malshe et al.

(10) Patent No.: US 10,407,352 B2
(45) Date of Patent: Sep. 10, 2019

(54) PLANT GROWTH PROMOTING COMPOSITION AND A PROCESS OF PREPARING THE SAME

(71) Applicant: NICHEM SOLUTIONS, Thane (W), Maharashtra (IN)

(72) Inventors: Vinod Chintamani Malshe, Mumbai (IN); Rajan Balkrishna Raje, Mumbai (IN); Rishikesh Ramakant Choudhari, Navi Mumbai (IN); Rupali Prakash Hande, Kalyan (IN)

(73) Assignee: NICHEM SOLUTIONS, Thane (W), Maharashtra (IN)

( * ) Notice: Subject to any disclaimer, the term of this patent is extended or adjusted under 35 U.S.C. 154(b) by 179 days.

(21) Appl. No.: 15/324,742

(22) PCT Filed: Feb. 25, 2016

(86) PCT No.: PCT/IN2016/050066
§ 371 (c)(1),
(2) Date: Jan. 9, 2017

(87) PCT Pub. No.: WO2016/135752
PCT Pub. Date: Sep. 1, 2016

(65) Prior Publication Data
US 2017/0190634 A1    Jul. 6, 2017

(30) Foreign Application Priority Data

Feb. 25, 2015    (IN) .................. 620/MUM/2015

(51) Int. Cl.
*C05D 9/02*    (2006.01)
*C05C 3/00*    (2006.01)
(Continued)

(52) U.S. Cl.
CPC .............. *C05D 9/02* (2013.01); *A01N 59/00* (2013.01); *C05B 17/00* (2013.01); *C05C 3/00* (2013.01); *C05G 3/0076* (2013.01); *C05G 3/06* (2013.01)

(58) Field of Classification Search
CPC .... C05C 3/00; C05D 9/02; C05G 3/06; C05G 3/0076; C05B 17/00; A01N 59/00
See application file for complete search history.

(56) References Cited

U.S. PATENT DOCUMENTS 3,274,249 A * 9/1966 Brunner ................. A61K 8/418
564/374
5,373,013 A * 12/1994 Hubele ................ A01N 43/653
514/275
(Continued)

FOREIGN PATENT DOCUMENTS

BG    10110579 A    7/2011
CN    101455208 A *    6/2009
(Continued)

OTHER PUBLICATIONS

Reddy, P. A. K.; International Search Report and Written Opinion of the International Searching Authority, issued in International Application No. PCT/IN2016/050066; dated Aug. 8, 2016; 8 pages.

*Primary Examiner* — Jennifer A Smith
(74) *Attorney, Agent, or Firm* — Ulmer & Berne LLP

(57) ABSTRACT

A stable composition is provided as plant growth promoters. The composition comprises of at least one source of weak acid, at least one free base and at least one penetration agent. Fertilizers and stabilizers can also be present as additional materials 5 in the plant growth promoting composition.

11 Claims, 3 Drawing Sheets

Effect of the compositions on Percentage survival rate of transplanted Spinach

(51) Int. Cl.
*C05G 3/00* (2006.01)
*A01N 59/00* (2006.01)
*C05B 17/00* (2006.01)
*C05G 3/06* (2006.01)

(56) References Cited

U.S. PATENT DOCUMENTS

2013/0280346 A1* 10/2013 Powers ............... A61L 2/206
                                                           424/663
2014/0256967 A1*  9/2014 Hicks ................. B01J 29/405
                                                           549/506

FOREIGN PATENT DOCUMENTS

| CN | 102096344 A | * | 12/2010 | |
|----|---|---|---|---|
| EP | 2578557 A1 | | 4/2013 | |
| WO | 2008069676 A2 | | 6/2008 | |
| WO | WO-2014120293 A1 | * | 8/2014 | ........... A61K 31/196 |

\* cited by examiner

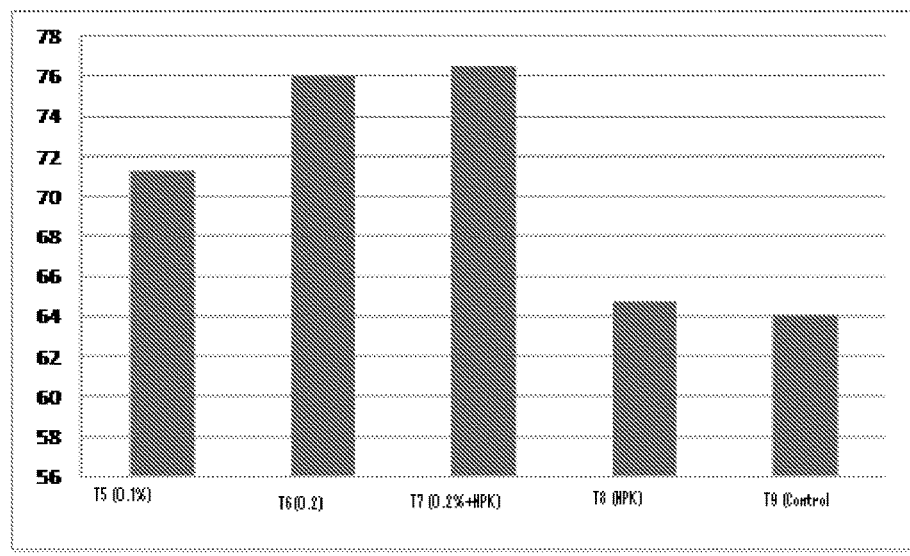
Figure 1: Effect of the compositions on Percentage survival rate of transplanted Spinach

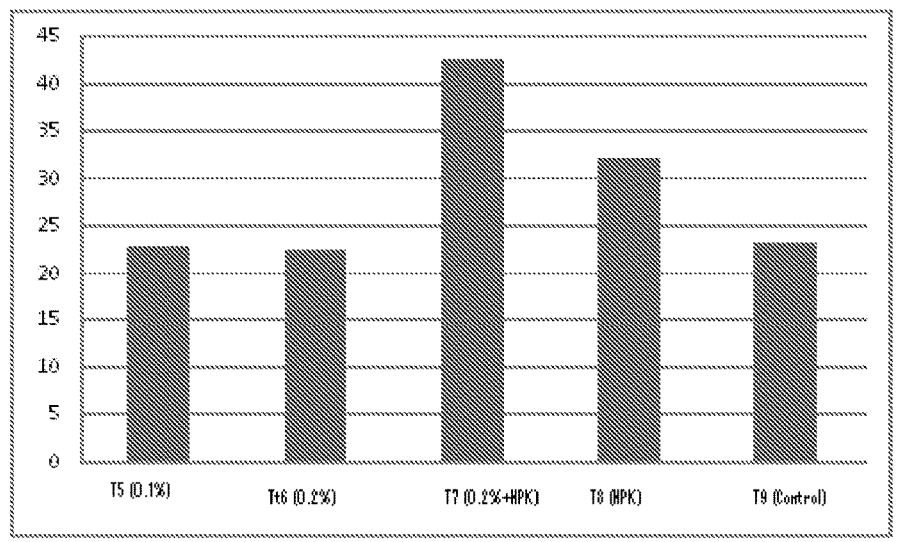
Figure 2: Effect of the compositions on spinach yield-Sigona (Kiambu County)

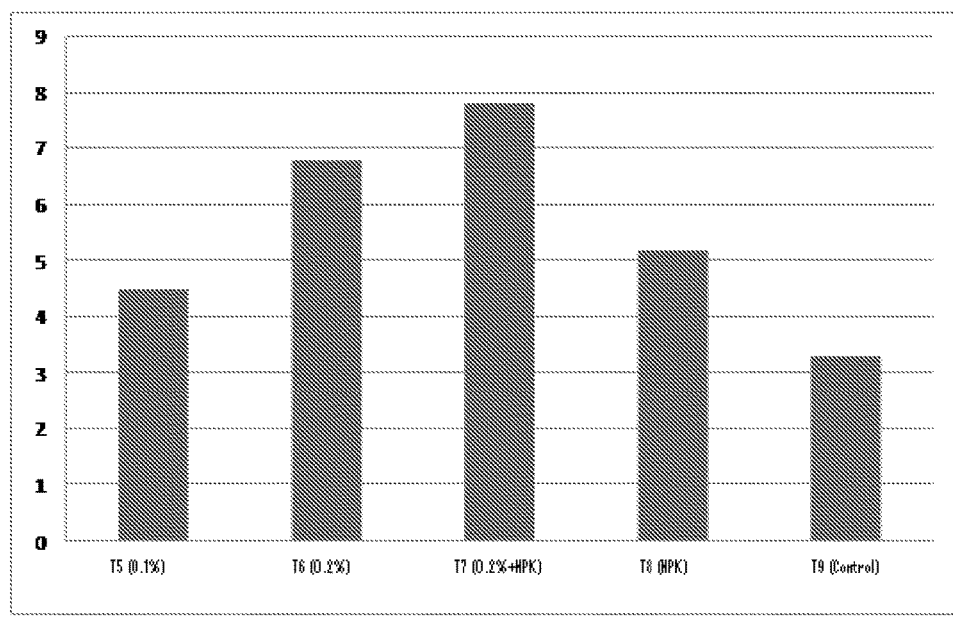
Figure 3: Effect of the compositions on French bean yield-Gatundu (Kiambu County)

PLANT GROWTH PROMOTING COMPOSITION AND A PROCESS OF PREPARING THE SAME

CROSS REFERENCE TO RELATED APPLICATIONS

This application is the United States national phase filing under 35 U.S.C. 371 of the corresponding international application number PCT/IN2016/050066, filed Feb. 25, 2016, which claims the priority benefit of Indian Patent Application Serial No. 620/MUM/2015, filed Feb. 25, 2015, each of which is hereby expressly incorporated by reference herein in its respective entirety.

FIELD OF THE INVENTION

The present invention relates to plant growth promoting composition and a process of preparing the same.

BACKGROUND OF THE INVENTION

Silicon is a beneficial nutrient for plants and is present in the form of silicic acid ($H_4SiO_4$) in soil, minerals and ocean water. In modern agricultural systems, the nutrient solutions are mostly deficient in silicic acid and the added silicates are unable to compensate this deficiency. Silicic acid is sometimes included in the formulations of nutrients, but is not stable enough to become bio-available because they are in the form of silicates which have poor solubility in water.

Further, silicates are not absorbed by organisms that help for plant growth. Probably, silicic acid is the highest bio-available silicon compound for diatoms, plants, animals and humans. In water, silicates and silica gel are slowly hydrolyzed into orthosilicic acid, which is poorly soluble and polymerizes quickly into small particles (non-colloidal material (non-opalescent, non-turbid). These polymerized structures directly aggregate into longer chains (still non-colloidal), leading to a real network (colloid; opalescent, turbid). This process results in the formation of a soft gel, which is poorly bio-available. Hence, to use silicon in an effective bio-available way, one has to prevent gel formation of the silicic acid. Conventionally known methods do not disclose the way to improve the bioavailability and efficacy of silicic acid as a plant growth promoter.

There is a need for a composition which increases bio-availability of silicic acid and is excellent for plant growth.

SUMMARY OF THE INVENTION

The present invention discloses a plant growth promoting composition comprising:
at least one source of weak acid;
at least one source of free base; and
at least one penetration agent.

Also disclosed is a process for preparing a composition for plant growth, which comprises mixing a source of weak acid, free base and penetration agent.

BRIEF DESCRIPTION OF THE DRAWINGS

FIG. 1 illustrates the effect of the compositions on survival rate of transplanted spinach.

FIG. 2 illustrates the effect of the compositions on yield of spinach.

FIG. 3 illustrates the effect of the compositions on yield of French beans.

DETAILED DESCRIPTION OF THE INVENTION

Accordingly, the present invention includes a plant growth promoting composition comprising at least one source of weak acid, at least one free base and at least one penetration agent.

Another embodiment of the present invention relates to a composition comprising at least one source of weak acid, at least one free base, at least one penetration agent and at least one fertilizer.

In a further embodiment, the composition comprises of at least one stabilizer.

The mole ratio of source of weak acid to free base in the composition is 1:1 to 1:8. Preferably, the mole ratio of source of weak acid to free base is 1:4.

Surprisingly, it was found that use of the composition not only improved plant growth but also resulted in excellent quality and yield of the fruits of fruit bearing plants. The combination of weak acid, free base and penetration agent was found to work synergistically thereby leading to an improvement in overall health of the plants. Additionally, the presence of fertilizer resulted in improved yield and survival rate of the plants.

The source of weak acid is selected from tetra ethyl ortho silicate, silicic acid, sodium silicate, sodium ortho silicate. The preferred source is sodium ortho-silicate. Various combinations of source of weak acids can also be used.

The composition comprises of 1 g/L or more source of weak acid. The preferred concentration of source of weak acid is 10-40 g/L, more preferably 20-30 g/L of the solution.

The free base used in the composition is a strong organic free base represented by the formula ($N^+R_1,R_2,R_3,R_4$) $OH^-$ wherein $R_1$, $R_2$, $R_3$ and $R_4$ are selected from the group consisting of methyl, ethyl, n-propyl, iso-propyl, n-butyl, iso-butyl or tert-butyl, benzyl selected from trimethylhydroxyethyl ammonium hydroxide (choline), tetra-butyl ammonium hydroxide, tetra-propyl ammonium hydroxide, benzyl triethyl ammonium hydroxide, tetra ethyl ammonium hydroxide, tetra methyl ammonium hydroxide, benzyl trimethyl ammonium hydroxide and combinations thereof. The preferred base is trimethylhydroxyethyl ammonium hydroxide.

Free base can be used in an amount of 10 to 900 g/L of the solution.

The penetration agent is selected from ethylene oxide, condensate of fatty alcohols, castor oil, fatty amine, ethoxylated silanol, trifluorodimethylpolysiloxane and combinations thereof. Preferably, ethoxylated silanol is incorporated in the composition.

The preferred amount of the penetration agent is 10-100 g/L of the solution.

The fertilizer is NPK (Nitrogen, Phosphorus and Potassium) as NH3:P2O5:K2O. The amount of fertilizer used depends on the crop and area of plot and is generally 50 kg of nitrogen, 30 kg of phosphorus and 30 kg of potassium per acre. The weight ratio of N:P:K can also be 1:1:1.

In a preferred embodiment of the invention, NPK fertilizer is directly added to the plant already treated with the composition as mentioned above.

Stabilizer is selected from monohydric alcohol, a polyhydric alcohol, a tertiary strong base, a humic acid, fulvic acid and combinations thereof. Monohydric alcohol is selected from methanol, ethanol, isopropanol, secondary and tertiary butanol, water soluble alcohols and combinations thereof.

Polyhydric alcohol is selected from the group consisting of glucose, sugar, fructose, polyethylene glycol, polypropylene glycol, sorbitol, mannitol, glycerol, neopentyl glycol, xyletol, co-polymers of ethylene glycol and propylene glycol and combinations thereof.

The strong base is selected from the group consisting of mono-ethanolamines, di-ethanolamines, tri-ethanolamines, hydroxylamine, hydroxyl ethyl amine, hydroxyl propyl amine, dimethyl ethanol amine, ethanol amine, propanol amine, tertiary amine hydroxide of general formula (R1,R2,R3,R4NOH) where R1, R2, R3, R4 are alkyl radicals from $C_1$ to $C_4$ for example tetra methyl amine hydroxide, tetra ethyl amine hydroxide, tetra butyl amine hydroxide, tetra propyl amine hydroxide and combinations thereof.

The preferred amount of the stabilizer is 10-100 g/L of the solution.

According to an embodiment of the present invention, the composition further comprises a solvent. According to a preferable embodiment of the present invention, the solvent is water. Advantageously, water is in the form of de-ionized water.

In certain embodiments, the composition may further comprise 0.5 to 60 g/L of acidic compounds such as molybdic acid and boric acid. Preferably, 1-10 g/L molybdic acid and 1-60 g/L boric acid is present in the composition.

In a preferred embodiment, the composition comprises of at least one source of weak acid, at least one free base, at least one penetration agent and at least one stabilizer.

The composition is in the form of a solution, powder.

The composition in the absence of NPK fertilizers is free from mono or higher inorganic cationic compounds. The cationic compounds are generally Group I, Group II, Group III, Group A and Group B elements of the periodic table. Examples include Li, Rb, Na, Mg, Ca, Ba, Sr, etc. Potassium is allowed as a cationic element since it is a component of fertilizers and is acceptable for plant life.

Another embodiment of the invention discloses a packaging comprising the composition containing at least one source of weak acid, at least one free base and at least one penetration agent.

As mentioned above, significant improvement in plant growth was found in plants treated with the composition. This can be attributed to an increased bioavailability of silicon in the form of silicic acid. The penetration agent reduces surface tension which is due to wax like layer on surface of plant. The reduction in surface tension allows penetration, maximum wetting and spreading of the composition in the plant surface, which results in increased bioavailability of silica. The composition is highly stable with absence of polymerization and gel formation. Silicic acid remains in a monomeric form.

Another aspect of the invention provides a process of preparing a plant growth promoting composition by treating source of a weak acid with a free base in the presence of a penetration agent. Further, stabilizers can also be added in the process followed by addition of water.

In an embodiment, the process of preparing a composition for plant growth composition further comprises adding fertilizers such as NPK fertilizers.

In an embodiment of the present invention, the composition is obtained by subjecting source of weak acid to strong acid cation exchange resins such as INDION 225 H, INDION 220 H, INDION 140, INDION 160 and directly discharging cation free acidic solution containing silicic acid in a solution containing an organic strong free base and penetration agent. In an alternate method, it is manufactured by dissolution of precipitated silica washed free of sodium, potassium or any other cation in organic strong free base and penetration agent. Silicic acid can also be prepared by hydrolysis of silicon tetra chloride in water containing large excess of organic free base, alkoxy esters of silicic acid such as tetra methyl silicate, tetra ethyl silicate, tetra propyl silicate, tetra isopropyl silicate or tetra isobutyl silicate.

It should be noted that the Applicant has not used any biological material in the invention. It should be understood that studies on plants were conducted to ascertain the efficacy of the disclosed composition and the plants as mentioned in the description are not the subject matter this invention. There is no biological material used as a subject matter of the invention. Hence, it is not necessary to obtain any permission from National Biodiversity Authority.

EXAMPLES

The following examples illustrate the invention but are not limiting thereof.

Example 1

Silicic acid was prepared by dissolving 76.66 g of sodium ortho silicate in 248 g of water and treating with a cation exchange resin, INDION 225 H. The elute containing 25 g silicic acid was discharged in a solution containing 72 g of choline, 37.5 g of ethoxylated silanol and 100 g of sorbitol. Demineralized water was added to make the quantity 1000 ml.

Example 2

Silicic acid was prepared from ion exchange of sodium from 76.66 g of sodium ortho-silicate with a cation exchange resin, INDION 225 H. The elute containing 25 g silicic acid was discharged in a solution containing 72 g of choline, 37.5 g of ethoxylated silanol, 100 g of mannitol and 66.6 g of methanol. 5 g of molybdic acid and 10 gm of boric acid was also added to the solution. Water was added to make the quantity 1000 ml.

Example 3

Silicic acid was prepared by hydrolysis of 37.5 g of tetraethyl ortho silicate with water in a solution containing 429.08 g of choline, 8.44 g of molybdic acid and 57.09 g of boric acid. The composition was diluted with 433.57 g of water.

Example 4

Silicic acid was prepared by hydrolysis of 208.33 g of tetraethyl ortho silicate with water in a solution containing 832.99 g of choline, 8.44 g of molybdic acid and 57.09 g of boric acid. The composition was diluted with 39.62 g of water.

Example 5

Silicic acid was prepared by hydrolysis of 107 g of tetraethyl ortho silicate with water in a solution containing 442 g of choline, 200 g of sorbitol. The composition was diluted with water.

Example 6

30 g of silica gel derived from potassium silicate (with 30% loss on ignition at 1000° C.) or 26 g ash obtained by burning rice husk (with 5% loss on ignition at 1000° C.) or 25 g of finely ground quartz mineral (99+% purity) was cooked with 72 g Choline (50% in water) at 150° C. under autogeneous pressure. The solution was cooled and filtered to remove any insoluble impurities. Other components such as boric acid and molybdic acid were then added to make up the other micro nutrients. The composition was made up with demineralized water to 1000 ml.

Example 7

Composition of Example 1 in varied concentrations as explained below was sprayed on various plants to which further NPK (50 kg nitrogen, 30 kg Phosphorus and 30 kg potassium per acre) was added. A combination of composition of Example 1 and NPK fertilizer gave beneficial results as elaborated in the Tables 6-9.

Investigations

A. Effect on Growth Parameters and Fruitfulness of Grape Vines.

Ten year old vines of Thompson Seedless grapes grafted on Dog Ridge rootstock were selected for the study. Experiment was set up in randomized block design (RBD) where there were five replications with vines per replication. The vines were trained to Flat Roof gable system of training with double cordons placed in horizontal direction. All the standard canopy management and cultural practices were followed since the foundation pruning. The experiment was initiated immediately after foundation pruning and continued after fruit pruning till harvest.

The composition of Example 1 in varying concentrations as given below was applied to the vines as spray using knapsack sprayer in different doses as mentioned below.

T1: 0.5 ml/L of the composition

T2: 1 ml/L of the composition

T3: 1.5 ml/L of the composition

T4: Control

During each pruning, the spraying schedule followed is as below.

|  | Foundation pruning | | Fruit pruning | |
| --- | --- | --- | --- | --- |
| Pruning date | Days | Growth stage | Days | Growth stage |
| First spray | $1^{st}$ | 6-7 leaves | $1^{st}$ | 6-7 leaves |
| Second spray | $17^{th}$ | Sub cane pinching | $16^{th}$ | Bunch emergence |
| Third spray | $31^{st}$ | 5-7 leaf after sub cane pinching | $30^{th}$ | Flowering |
| Fourth spray | $47^{th}$ | Shoot maturity started | $44^{th}$ | Berry setting |
| Fifth spray | $63^{rd}$ | Matured shoot | $52^{nd}$ | 8-10 mm berry |
| Sixth spray | $81^{st}$ | Matured shoot | $60^{th}$ | 12 mm berry |
| Seventh spray |  | Matured shoot | $67^{th}$ | 14-16 mm berry |

Following observations were recorded—

Fruit Pruning

1. Vegetative Growth:

The observations on shoot length, leaf area, cane diameter and cane maturity were recorded at 90 days after pruning. Shoot length was measured with measuring tape while the shoot diameter was measured using Vernier calliper. Leaf area was measured using portable leaf area meter (model CI-203 Leaf area meter, CID. Inc. USA). The leaf tissues were collected at 120 days for chlorophyll content in leaf as per the method suggested by Barnes et al., (1992). Representative leaf (fifth and sixth leaf from apex) samples from the vines were obtained in triplicate. Immediately after sampling, the samples were washed with deionized water, air-dried and stored at −200° C. till extraction.

2. Gas Exchange Parameters:

Photosynthetic activities, stomatal conductance and transpiration rate was recorded at berry setting stage during 10.30 am to 11.30 am. Newly matured leaf that is fifth leaf from the apex was selected to record the photosynthetic rate. Portable infrared gas analyser (model Li 6400, LI-COR Biosciences. Nebraska, USA) was used to record the photosynthetic activities of leaf. On each plant, five leaves were selected to record the photosynthetic rate and three readings on each leaf were taken and the mean values were calculated by averaging.

3. Quality Parameters:

The observations on TSS, Acidity, Juice pH, average berry diameters, Berry weight, etc. were recorded after harvesting bunches randomly among the different treatments. Total soluble solids were recorded using refractometer model ERMA, Japan, 4. Nutrient Status:

The petioles opposite to the bunch and the leaf at $5^{th}$ position were collected randomly from each treatment. The status of major nutrients in leaf and petiole of vines treated with different doses of the composition were studied. The fully matured shoots were collected at 120 days after pruning. After washing with distilled water and oven drying, the shoots were then subjected to grinding, sieved and the fine powder was used for analysis of major nutrients. Among the nutrients, nitrogen was estimated using nitrogen auto analyser by Kjeldahl method using Gerhardt Distillation Unit (Vapodest 30). Phosphorous content was estimated using UV-visible spectrophotometer, Evolution, 201, Thermo Scientific, USA and potash content in leaf was estimated using digital flame photometer, JENWAY, UK. The nutrient content in leaf was expressed as % dry weight basis.

5. Other Studies (Yield Per Vine and Biochemical Status of Vines, Etc.):

Estimation of carbohydrate and starch was done by Anthrone method. Reducing sugar was estimated by the dinitrosalicylic acid (DNSA) method described by Lowry et al., (1951). Total phenolics content was estimated using Folin-Ciocalteu reagent and by measuring the absorbance of the reaction mixture at 650 nm (Singleton and Rossi, 1965). The results obtained were expressed as catechol equivalent (mg/g) of the crushed sample.

1a. Effect of T1, T2, T3 on Growth Parameters:

The observations recorded on various growth parameters under each treatment are presented in table 1. All the doses of the composition T1 (0.5 ml/l), T2 (1.0 ml/l) and T3 (1.5 ml/l) showed significant increase in all the growth parameters such as shoot length, shoot diameter, and inter nodal length over control except that in case of T1 where the shoot length was at par with control.

The leaf area plays an important role in storing the food material in different parts of a vine through the process of photosynthesis. This helps in development of a bunch that is called as sink. Hence, the leaf becomes the source for food material required for a developing bunch. Significant differences were recorded for leaf area among the different treatments of T1, T2, T3 and T4. T3 application showed significantly higher leaf area as compared to T4 (control). Days required for cane maturity ranged between 80-84 days and were on par except T3 showed significantly less number of days (80 days) over other treatments including the T4.

TABLE 1

Effect of T1, T2, T3 and T4 composition on growth parameters.

| Treatments | Shoot length (cm) | Shoot diameter (cm) | Inter nodal length (cm) | Leaf area (cm$^2$) | Days to cane maturity |
|---|---|---|---|---|---|
| T1 | 41.5 | 6.10 | 5.0 | 103.48 | 84 |
| T2 | 47.20 | 5.77 | 4.7 | 102.05 | 83 |
| T3 | 55.30 | 6.24 | 5.2 | 193.2 | 80 |
| T4 | 40.30 | 4.34 | 4.4 | 125.7 | 84 |
| CV % | 2.53 | 2.26 | 2.01 | 3.55 | 1.58 |
| LSD 5% | 1.61 | 0.17 | 0.13 | 6.40 | 1.81 |

1b. Effect of T1, T2, T3 and T4 on Berry Quality and Yield Parameters:

The data collected on various berry quality parameters are given in table 2. The berry diameter and weight contributes the average bunch weight and also the total yield/vine. In addition, bunches with bold berries are considered as quality grapes. Significant variation was observed for berry diameter among the different treatments studied. The berry diameter ranged from 17.34 mm in T2 treated vines to 19.64 mm in T3 treated vines. The differences for berry diameter among T1 treatment and control were at par. The increase in berry diameter also contributed for average bunch weight. Higher bunch weight was recorded in T3 treatment (360.40 g) than the lowest in T4 and T1 treatment. In general, all the treatments were found superior over T4 in respect to berry diameter and average bunch weight. Considering the bunch and berry quality, the treatment of T3 was found to be superior in respect to average berry diameter and bunch weight. Though the differences for TSS were statistically significant, the variations among the treatments were at par. With the increase in berry size, the TSS was found to be reduced. The TSS ranged from 20.4 to 22.3° Brix whereas the berry diameter reduced from 19.64 mm to 17.34 mm. The yield per vine differed significantly among the treatments studied. The application of T1, T2, T3 recorded higher yield/vine as compared to the untreated control T4. The treatment with T3 recorded higher yield of 16.5 kg/vine compared to 9.3 kg/vine in control.

1c. Effect of T1, T2, T3 and T4 on Biochemical Status:

The observations recorded on various biochemical constituents are presented in table 3. The carbohydrates contents of grape berries varied significantly with the different treatments of the composition. The highest contents of carbohydrates were found with the application of T3 (45.08 mg/g) compared to the untreated control T4 (24.54 mg/g). The increase in carbohydrate content is due to increased canopy with increase in leaf area in the treatment with varying doses of composition. The concentration of reducing sugar in the grape berries varied significantly among the different treatments. However, the concentration was more in T4 than in T1 and T2 treatment. The same trend was also observed for starch and proteins. Total phenol contents in grape berries were highest in T3 (5.95 mg/g) than the lowest in control treatment T4 (1.32 mg/g).

TABLE 3

Effect of T1, T2, T3 and T4 on Biochemical parameters

| Treatment | Total Carbohydrate (mg/g) | Reducing sugar (mg/g) | Protein (mg/g) | Starch (mg/g) | Phenols (mg/g) |
|---|---|---|---|---|---|
| T1 | 27.98 | 8.25 | 10.56 | 10.17 | 2.62 |
| T2 | 40.10 | 5.35 | 4.06 | 4.61 | 1.59 |
| T3 | 45.08 | 7.53 | 5.07 | 7.54 | 5.95 |
| T4 | 24.54 | 10.10 | 13.83 | 3.28 | 1.32 |
| CV % | 3.13 | 2.91 | 4.64 | 3.46 | 3.97 |
| LSD 5% | 1.49 | 0.31 | 0.54 | 0.30 | 0.16 |

1d. Effect of T1, T2, T3 and T4 on Photosynthetic Rate

The observations recorded on photosynthetic parameters are presented in table 4. The photosynthetic parameters such as net photosynthesis and transpiration rate varied significantly among the different treatments studied. In the present study, chlorophyll contents and photosynthesis rate was increased proportionately.

TABLE 4

Effect of T1, T2, T3 and T4 on leaf chlorophyll and photosynthesis

| Treatment | Chlorophyll a (mg/g) | Chlorophyll b (mg/g) | Total Chlorophyll (mg/g) | Photosynthesis ($\mu$mol/cm$^2$/s) | Transpiration rate (mmol $H_2O$ m$^{-2}$S$^{-1}$) |
|---|---|---|---|---|---|
| T1 | 2.49 | 0.68 | 3.23 | 8.482 | 1.366 |
| T2 | 2.22 | 0.66 | 2.97 | 8.764 | 1.891 |
| T3 | 2.38 | 0.62 | 3.08 | 7.964 | 2.076 |
| T4 | 1.99 | 0.54 | 2.64 | 8.403 | 1.930 |

TABLE 2

Effect of T1, T2, T3 and T4 on berry quality and yield parameters

| Treatment | No of Bunch/vine | No. of bunches per sq meter | No of Berries/bunch | Av bunch wt (gm) | 50 berry wt (gm) | Berry dia (mm) | Berry (mm) | TSS (°Brix) | TA (g/l) | pH | Yield/vine (kg) |
|---|---|---|---|---|---|---|---|---|---|---|---|
| T1 | 33 | 5.89 | 77 | 280.0 | 195 | 18.93 | 19.9 | 21.5 | 6.6 | 3.67 | 9.45 |
| T2 | 38 | 6.7 | 74 | 275.1 | 202 | 17.34 | 21.4 | 22.3 | 7.1 | 3.61 | 12.1 |
| T3 | 45 | 8.0 | 78 | 360.4 | 242 | 19.64 | 22.7 | 20.4 | 6.4 | 3.65 | 16.5 |
| T4 | 35 | 6.25 | 75 | 280.5 | 199 | 18.10 | 20.2 | 21.4 | 6.9 | 3.65 | 9.3 |
| CV % | 2.48 | 2.48 | 1.80 | 2.47 | 2.30 | 1.91 | 2.03 | 1.76 | 1.53 | 1.70 | 3.32 |
| LSD 5% | 1.29 | 0.23 | 1.88 | 10.188 | 6.62 | 0.49 | 0.59 | 0.52 | 0.14 | — | 0.54 |

TABLE 4-continued

Effect of T1, T2, T3 and T4 on leaf chlorophyll and photosynthesis

| Treatment | Chlorophyll a (mg/g) | Chlorophyll b (mg/g) | Total Chlorophyll (mg/g) | Photosynthesis (μmol/ cm$^2$/s) | Transpiration rate (mmol H$_2$O m$^{-2}$S$^{-1}$) |
|---|---|---|---|---|---|
| CV % | 1.93 | 2.06 | 1.87 | 1.59 | 2.33 |
| LSD 5% | 0.06 | 0.02 | 0.08 | 0.18 | 0.06 |

1e. Effect of T1, T2, T3 and T4 on Nutrient Status in Vine

The data on status of various nutrient contents in leaf blade and also in petiole studied during the 45$^{th}$ day after fruit pruning is presented in Table 5. In general, it was observed that the amount of nutrient content was higher in petiole than in the leaf blade. The petiole is considered as an indicator for nutrients status of grapevine. Among the major nutrients, phosphorus plays an important role in improving fruitfulness after back pruning and increase in berry size after fruit pruning. In the present investigation, higher amount of phosphorus in petiole was correlated with more fruitful canes per vine. The vines treated with T3 recorded higher amount of P in shoot petiole. The same trend was also recorded for Phosphorus content in leaf blade. Higher amount of Mg was also recorded in the same treatment.

TABLE 5

Effect of T1, T2, T3 and T4 on nutrient status in vine

| Treatments | N (%) | P (%) | K (%) | Na (%) | Ca (%) | Mg (%) | Mn (%) | Fe (ppm) | Cu (ppm) | Zn (ppm) |
|---|---|---|---|---|---|---|---|---|---|---|
| Nutrient status in leaf | | | | | | | | | | |
| T1 | 0.73 | 0.21 | 2.02 | 1.89 | 2.88 | 1.35 | 95.20 | 57.90 | 14.50 | 86.20 |
| T2 | 0.70 | 0.25 | 1.98 | 2.26 | 2.67 | 1.83 | 99.40 | 54.0 | 13.2 | 78.20 |
| T3 | 0.70 | 0.27 | 1.77 | 2.33 | 2.44 | 1.74 | 113.3 | 68.30 | 15.1 | 83.40 |
| T4 | 0.64 | 0.22 | 1.70 | 2.34 | 2.59 | 1.70 | 104.2 | 78.8 | 16.5 | 89.60 |
| Nutrient status in petiole | | | | | | | | | | |
| T1 | 0.81 | 0.31 | 2.41 | 2.43 | 2.01 | 1.78 | 102.30 | 70.50 | 12.40 | 74.60 |
| T2 | 0.87 | 0.34 | 2.53 | 2.57 | 2.05 | 1.76 | 94.64 | 76.30 | 16.10 | 91.20 |
| T3 | 0.87 | 0.38 | 2.38 | 2.53 | 2.23 | 1.99 | 115.60 | 67.50 | 12.90 | 79.80 |
| T4 | 0.90 | 0.31 | 2.45 | 2.21 | 2.11 | 2.13 | 103.40 | 56.30 | 14.90 | 84.20 |

B. Effect of the Compositions on Germination Rate of French Beans and Spinach

A field trial was carried out in six ecologically different locations namely Mwea, Sigona, Gatundu (Central region), Kilifi (Coastal region), Molo and Eldoret (Rift Valley region) to determine the effect of the compositions on pod and leaf yield of French beans and spinach respectively. These sites were selected because of the need to replicate the trial in different ecological regions. Three treatments of the composition of Example 1 (0.1, 0.2% and 0.2%+NPK) alongside NPK alone and untreated control were evaluated. These treatments were T5=0.1% of the composition
T6=0.2% of the composition
T7=0.2% of the composition+NPK (nitrogen, phosphorus and potassium)
T8=NPK fertilizer
T9=control (untreated).

The experiment was laid out in a complete randomized design having three replications. Three harvests were done, data recorded and then analyzed appropriately. Data collected revealed that T6 at concentration of 0.2% increased the germination rate and T7 had significant effect on spinach and French bean yield in different localities.

Field experiments were carried out in Kirinyaga County (Mwea), Kiambu County (Sigona), Kiambu County (Gatundu), Kilifi county (Pwani university), Nakuru County (Molo) and Uasin Gishu County (University of Eldoret). All the trials were carried out in the open field under drip irrigation except in Mwea the experiment was carried out under fallow irrigation.

The French bean variety tested was Cv. Soria, while the spinach variety tested across all the regions was Cv. Giant Noble. For Mwea each plot (treatment unit) measured 5 m$^2$ while in all the other trials where drip was carried the field dimensions were 26.5 m×15.5 m with 29 drip lines 2 ft apart from each other running the entire length of the field. Each treatment plot had a length of 5 meters and 6 feet (2 m) wide. There were four replicates per treatment.

T5, T6 and T7 were applied using a knapsack sprayer with a medium spray nozzle while the NPK treatments (T8) were applied by placement method at the base of the plants. Where NPK was applied this was done at top dressing and not at planting as all the other treatments. The trial was allowed to run until completion of 55 days in the case of French beans and 60 days in the case of Spinach. Standard agronomic practices for French beans and spinach were followed. The design of the experiment was randomized complete block design replicated 3 times. An important observation was that the status of soil physiochemical properties and soil types may determine the effectiveness of the composition as of the six (6) sites, two (2) were selected and soil physical chemical properties determined.

The data obtained was subjected to analysis of variance using a statistical package Genstart 12$^{th}$ edition software program. Significant differences between means were separated by Tukey test at p≤0.05.

From the study it can be seen that the composition either alone (T5 or T6) or in combination with NPK fertilizer (T7) has growth promoting abilities. For instance when applied on Spinach at transplanting, plots treated with T6 improved the survival rate in Sigona (Kiambu County), Mwea (Kirinyaga County), Eldoret Uasin Gishu County, Gatundu, (Kiambu County), and Molo (Nakuru County).

It was found that the composition T7 had the maximum impact on survival rate and yield of spinach and French beans. T5 and T6 also gave beneficial results.

FIG. 1 shows the effect of T5, T6, T7, T8 and T9 on survival rate of transplanted spinach. It can be seen from FIG. 1 that spinach treated with T7 survived the most when compared with spinach treated with T5, T6, T8 and T9. Nonetheless, survival rates with T5 and T6 were also acceptable, which indicates that the composition of the either alone or in combination with fertilizers is beneficial for plant growth.

FIG. 2 shows the effect of T5, T6, T7, T8 and T9 on yield of spinach. Spinach treated with T7 gave the maximum yield.

FIG. 3 shows the effect of T5, T6, T7, T8 and T9 on yield of French bean. French beans treated with a combination of T7 gave the maximum yield. Also, French beans treated with T5 and T6 gave high yields.

Table 6 and Table 7 elucidate the effect of the T5, T6, T7, T8 and T9 on the yield of spinach and French beans respectively. On the effect on yield of Spinach, T7 was the most effective across all the six ecological regions followed by T6 alone. T5 generally produced lower yield but higher than T9 in all the treatments. The same trends were observed in the yield of French beans.

TABLE 6

Effect of T5, T6, T7, T8 and T9 on Yield (Kg) of Spinach

| Treatment\Locality | Mwea | Sigona | Kilifi | Eldoret | Gatundu | Molo |
|---|---|---|---|---|---|---|
| T5 (0.1%) | 10.3 ± 0.3b | 22.8 ± 0.9c | 20.5 ± 0.9c | 24.3 ± 0.5c | 23 ± 1.2c | 22.3 ± 0.6c |
| T6 (0.2%) | 13.8 ± 0.7a | 22.5 ± 1.0c | 20.3 ± 0.6c | 22.5 ± 1d | 24.5 ± 0.6c | 21.5 ± 0.6c |
| T7 (0.2% + NPK) | 13.2 ± 0.5a | 43.5 ± 0.8a | 34.5 ± 1.3a | 43.3 ± 0.6a | 40 ± 1.9a | 34.5 ± 1.3a |
| T8 (NPK (Standard rate) | 13 ± 0.4a | 32 ± 0.9b | 30.8 ± 1.1b | 32 ± 1.5b | 35 ± 1.7b | 30.8 ± 0.8b |
| T9 (Untreated Control) | 10 ± 0.7b | 23.3 ± 1.1d | 16 ± 2d | 21.5 ± 0.9d | 24 ± 1.2c | 18.0 ± 1.1d |

Means obtained by averaging 4 replicates
Means within a column followed by the same letter are not significantly different at $P \leq 0.05$

TABLE 7

Effect of T5, T6, T7, T8 and T9 on yield of French beans

| Treatment\Locality | Mwea | Sigona | Kilifi | Eldoret | Gatundu | Molo |
|---|---|---|---|---|---|---|
| T5 (0.1%) | 10.5 ± 0.3b | 4 ± 0.4c | 4.5 ± 1.1b | 4.8 ± 0.5d | 4.5 ± 0.2d | 3.8 ± 0.8c |
| T6 (0.2%) | 9.8 ± 0.6c | 5.3 ± 0.3a | 5.5 ± 1.0b | 6.5 ± 0.3a | 6.8 ± 0.3b | 5.3 ± 0.5a |
| T7 (0.2% + NPK) | 11.3 ± 0.5b | 5.5 ± 0.4a | 7.3 ± 0.8a | 6 ± 0.4c | 7.8 ± 0.3a | 4.8 ± 0.3b |
| T8 (NPK (Standard rate) | 13.8 ± 0.2a | 5.0 ± 0.4b | 7.3 ± 0.4a | 6.3 ± 0.4b | 5.3 ± 0.5c | 4.8 ± 0.5b |
| T9 (Untreated Control) | 8.8 ± 0.5d | 3.5 ± 0.3d | 3.5 ± 0.3c | 3.5 ± 0.2e | 3.3 ± 0.3e | 3.0 ± 0.4d |

Means obtained by averaging 4 replicates
Means within a column followed by the same letter are not significantly different at $P \leq 0.05$ Table 8 and Table 9 illustrate the germination capacity of spinach and French beans. In Mwea T6 had the highest effect on germination followed by T5 all significantly different (P>0.05). The same trend was observed in Sigona where T6 0.2% and T7 produced the best results followed by T5 all significantly different from the control (P≤0.05). The same trend was observed in Kilifi, Kilifi County, coastal Kenya (Table 9). Generally in terms of germination, T6 increased the germination rate of French beans.

TABLE 8

Germination Percentages (%) of Spinach when subjected to various treatments

| Treatment\Locality | Mwea | Sigona | Kilifi | Eldoret | Gatundu | Molo |
|---|---|---|---|---|---|---|
| T5 (0.1%) | 71.3 ± 0.4b | 73 ± 1.2b | 63.8 ± 0.5b | 75 ± 1.1a | 74.5 ± 0.8a | 77.5 ± 1.2a |
| T6 (0.2%) | 76.0 ± 0.4a | 78.8 ± 0.5a | 67.8 ± 0.6a | 76.8 ± 0.9a | 75.3 ± 0.9a | 78.8 ± 0.5a |
| T7 (0.2% + NPK) | 76.5 ± 0.7a | 69 ± 0.c | 59 ± 1.0c | 69.7 ± 0.5c | 66.2 ± 2.0b | 70.0 ± 0.6b |
| T8 (NPK (Standard rate) | 64.8 ± 0.5c | 69 ± 0.4c | 59.7 ± 0.8c | 69.5 ± 2.0c | 64.8 ± 0.5b | 70.3 ± 0.6b |
| T9 (Untreated Control) | 64 ± 0.9c | 68.2 ± 0.5d | 60.0 ± 0.9c | 70.0 ± 0.8c | 64.0 ± 0.9b | 69.2 ± 0.9b |

Means obtained by averaging 4 replicates
Means within a column followed by the same letter are not significantly different at $P \leq 0.05$

TABLE 9

Germination Percentages (%) of French Beans when subjected to the various treatments

| Treatment\Locality | Mwea | Sigona | Kilifi | Eldoret | Gatundu | Molo |
|---|---|---|---|---|---|---|
| T5 (0.1%) | 64.5 ± 0.8b | 51.3 ± 0.8b | 64.5 ± 0.6b | 74.5 ± 0.6a | 73.2 ± 1.1b | 65 ± 0.8c |
| T6 (0.2%) | 72.5 ± 1.2a | 56.5 ± 1.2a | 72.5 ± 1.0a | 75 ± 0.5a | 73.7 ± 1.6b | 68.5 ± 1.2b |
| T7 (0.2% + NPK) | 62.8 ± 0.5c | 56.8 ± 0.5a | 73.3 ± 1.0a | 75 ± 1.1a | 76.5 ± 0.9a | 65 ± 0.5c |
| T8 (NPK (Standard rate) | 63.5 ± 0.5c | 41.2 ± 0.5c | 55 ± 0.5c | 74.8 ± 1.1a | 72.3 ± 1.0b | 72.3 ± 1a |
| T9 (Untreated Control) | 63.3 ± 0.6c | 49.5 ± 0.6d | 52.5 ± 0.6d | 52.5 ± 1.0b | 52.5 ± 1.0c | 52.5 ± 0.2d |

Means obtained by averaging 4 replicates
Means within a column followed by the same letter are not significantly different at $P \leq 0.05$ There was no phytotoxicity observed. Also, better water retention was observed with the use of T5, T6 and T7.

It can be concluded that the composition of the present invention has growth promoting abilities either alone or in combination with NPK. Also, no phytotoxicity was observed when the composition (T5 and T6) was used alone or in combination with NPK (T7).

The invention claimed is:

1. A plant growth promoting composition, the composition comprising:
    at least one source of weak acid selected from a group consisting of tetra ethyl ortho silicate, silicic acid, sodium silicate, sodium ortho silicate, and combinations thereof;
    at least one free base comprising a strong organic base selected from a group consisting of trimethylhydroxyethyl ammonium hydroxide, tetra-butyl ammonium hydroxide, tetra-propyl ammonium hydroxide, benzyl triethyl ammonium hydroxide, tetra ethyl ammonium hydroxide, tetra methyl ammonium hydroxide, benzyl trimethyl ammonium hydroxide, and combinations thereof;
    at least one penetration agent selected from a group consisting of ethylene oxide, a condensate of fatty alcohols, castor oil, a fatty amine, ethoxylated silanol, trifluorodimethylpolysiloxane, and combinations thereof; and
    at least one stabilizer is selected from monohydric alcohol, a polyhydric alcohol, a tertiary strong base, a humic acid, fulvic acid and combinations thereof.

2. The composition as claimed in claim 1 comprising NPK fertilizer.

3. The composition as claimed in claim 1, wherein the polyhydric alcohol is selected from glucose, sugar, fructose, polyethylene glycol, polypropylene glycol, sorbitol, mannitol, glycerol, neopentyl glycol, xyletol, co-polymers of ethylene glycol, propylene glycol and combinations thereof.

4. The composition as claimed in claim 1, wherein the monohydric alcohol is selected from methanol, ethanol, isopropanol, secondary and tertiary butanol, water soluble alcohols and combinations thereof.

5. The composition as claimed in claim 1, wherein the strong base is selected from mono-ethanolamines, di-ethanolamines, tri-ethanolamines, hydroxylamine, hydroxyl ethyl amine, hydroxyl propyl amine, dimethyl ethanol amine, ethanol amine, propanol amine, tertiary amine hydroxide of general formula (R1,R2,R3,R4NOH) where R1, R2, R3, R4 are alkyl radicals from $C_1$ to $C_4$ such as tetra methyl amine hydroxide, tetra ethyl amine hydroxide, tetra butyl amine hydroxide, tetra propyl amine hydroxide and combinations thereof.

6. The composition as claimed in claim 1, further comprising a solvent, wherein the solvent is deionized water.

7. The composition as claimed in claim 1, further comprising an acidic compound, wherein the acidic compound comprises of molybdic acid, boric acid and combinations thereof.

8. The composition as claimed in claim 1, wherein the composition is in the form of a solution.

9. The composition as claimed in claim 1, wherein the mole ratio of weak acid to free base is 1:1 to 1:8.

10. The composition as claimed in claim 1 comprising
    1 g/L or more of the source of weak acid;
    10 to 900 g/L of the free base;
    10-100 g/L of the penetration agent; and
    10-100 g/L of the stabilizer.

11. The composition of claim 7 comprising 1-10 g/L molybdic acid and 1-60 g/L boric acid.

\* \* \* \* \*